United States Patent [19]
Pearson et al.

[11] Patent Number: 5,364,363
[45] Date of Patent: Nov. 15, 1994

[54] RECTAL ADMINISTRATOR

[75] Inventors: William R. Pearson, Laurel, Md.; N. Lawrence Dalling, Cross Junction, Va.

[73] Assignee: Survival Technology, Inc., Rockville, Md.

[21] Appl. No.: 87,968

[22] Filed: Jul. 8, 1993

[51] Int. Cl.$^5$ .............................................. A61M 5/20
[52] U.S. Cl. .................................... 604/136; 604/218; 604/275
[58] Field of Search ...................... 604/133-, 604/136, 218, 275

[56]         References Cited
         U.S. PATENT DOCUMENTS

| | | |
|---|---|---|
| 627,658 | 6/1899 | Smither . |
| 1,015,253 | 1/1912 | Weaver et al. ........................ 604/135 |
| 1,175,129 | 3/1916 | Crittenden ........................... 604/135 |
| 1,775,329 | 9/1930 | Sprague . |
| 1,853,260 | 4/1932 | Crossett ............................... 604/218 |
| 4,846,801 | 7/1989 | Okuda et al. . |
| 4,968,302 | 11/1990 | Schluter et al. ...................... 604/135 |
| 5,041,088 | 8/1991 | Ritson et al. ......................... 604/135 |
| 5,085,641 | 2/1992 | Sarnoff et al. ....................... 604/135 |
| 5,085,642 | 2/1992 | Sarnoff et al. ....................... 604/134 |
| 5,102,393 | 4/1992 | Sarnoff et al. ....................... 604/134 |

Primary Examiner—Jerome L. Kruter
Attorney, Agent, or Firm—Cushman, Darby & Cushman

[57]         ABSTRACT

A rectal administrator comprises a body having an administrative portion adapted to be inserted into a subject's rectum. A charge of medicament is disposed within the body, and the administrative portion has at least one passage through which the medicament can exit the body. A plunger is disposed in the body and is movable from a first position to a second position within the body to dispense the medicament from the body through the at least one passage. A releasable energy source is mounted within the body so as to be released in response to a predetermined actuating procedure. The releasable energy source moves the plunger from the first position to the second position to dispense the medicament from the body through the at least one passage when released in response to the predetermined actuating procedure.

25 Claims, 2 Drawing Sheets

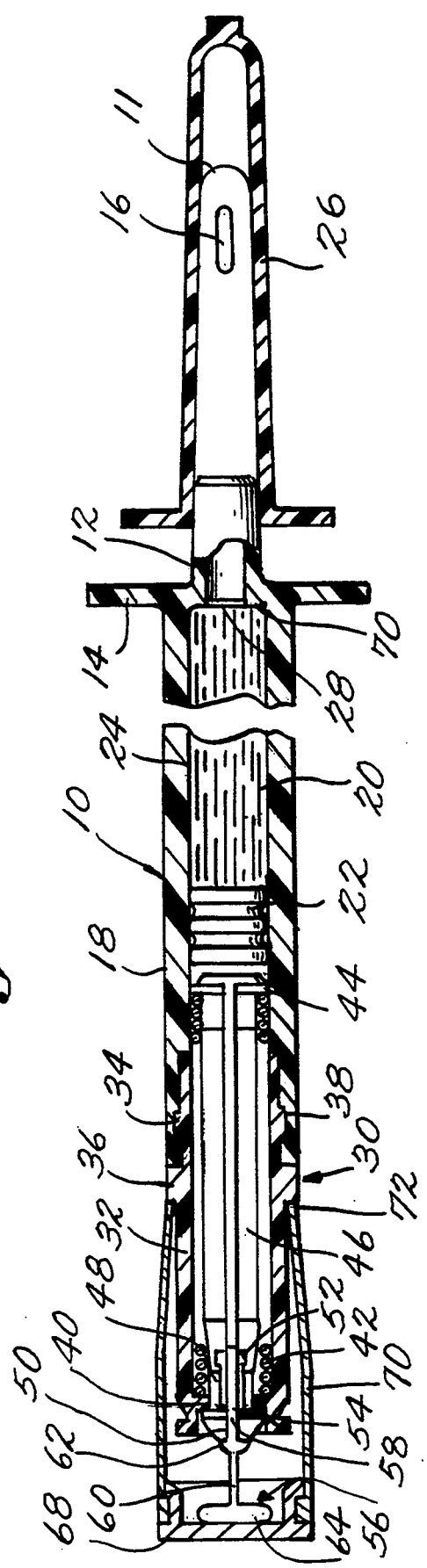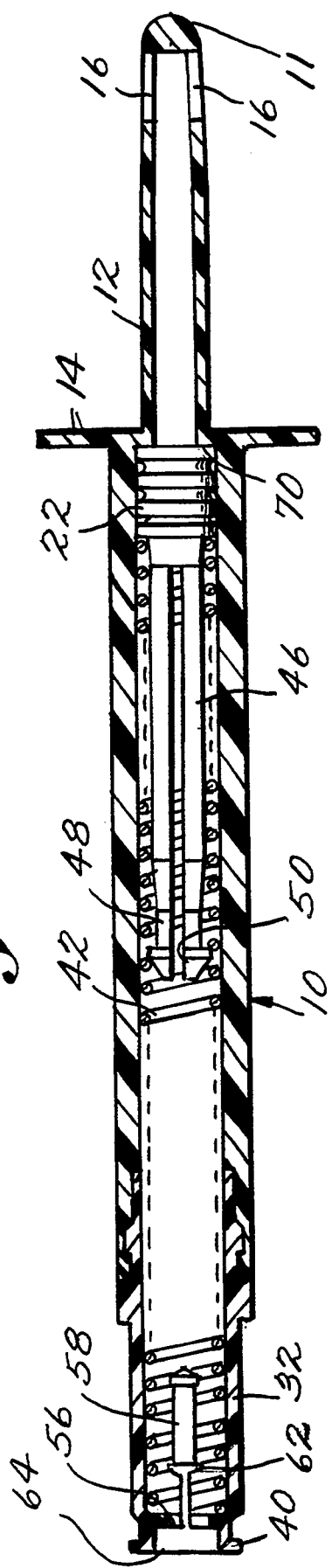

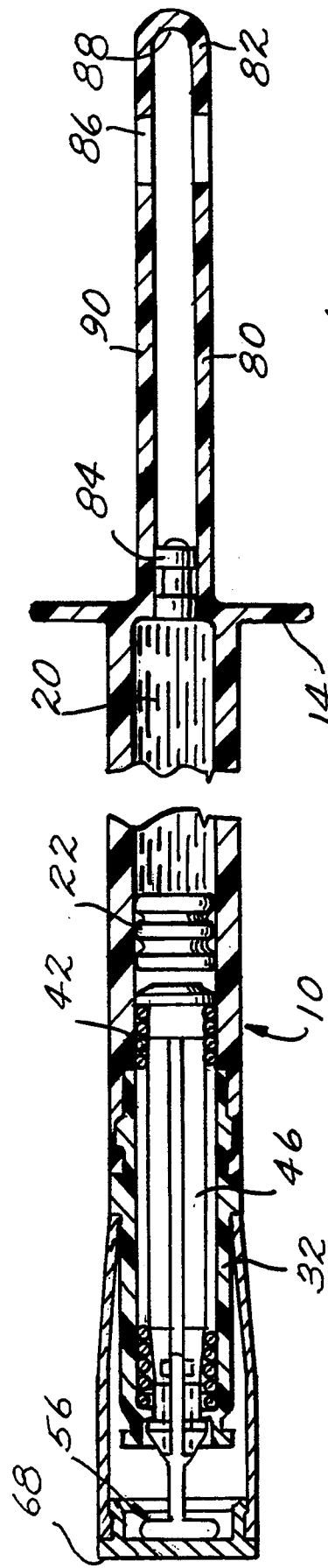
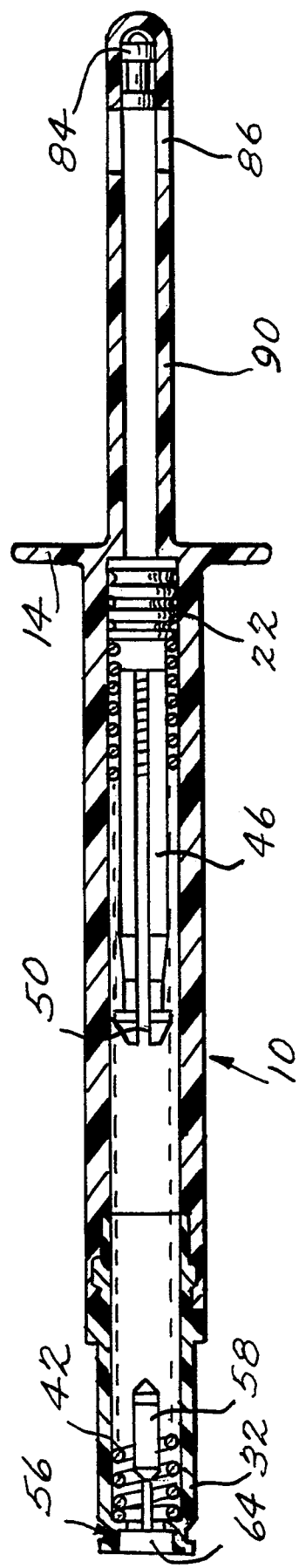

RECTAL ADMINISTRATOR

BACKGROUND OF THE INVENTION

FIELD OF THE INVENTION

This invention relates generally to automatic injectors, and more specifically to automatic injectors adapted for injecting a medicament into the rectum of a subject.

While the rectal administrator of the present invention can be used to treat any type of physical ailment which can be treated by injecting a medicament into the rectum, the present invention is primarily concerned with the treatment of febrile seizures. Febrile convulsions are the most common type of seizure occurring in children. In fact, such seizures occur in about 2 to 4 percent of all children. In addition, approximately one third of those children who suffer a febrile seizure also have at least one relapse.

Recent studies have shown the benefits of treating febrile convulsions with rectal diazepam (while other anti-convulsant drugs, such as phenobarbitone, valproate, and clonazepam have also been rectally administered to treat febrile convulsions, heretofore, diazepam has been the drug of choice). It can be appreciated that during an acute febrile seizure, it is extremely important for the diazepam to be administered as quickly as possible. Though febrile convulsions generally carry good prognosis, the attacks can lead to permanent neurological damage and even death.

Abundant pharmacokinetic evidence suggests that rectal diazepam in solution may effectively treat both ongoing and acute seizures and be an advantageous alternative to i.v. diazepam. Not only is rectal administration less painful and easier to administer, but it has been shown that absorption of diazepam is more rapid when administered rectally than when administered intravenously. With rectal administration of diazepam, presumed anticonvulsant levels are attained within minutes, especially in infants and small children.

It can be appreciated, therefore, that a limiting factor in the effectiveness of rectal diazepam is the ease and speed by which it can be administered.

Thus far, the typically available rectal administrator, as disclosed in U.S. Pat. Nos. 627,658, 4,846,801, and 1,775,329, has been manufactured for non-emergency treatment of hemorrhoids, fissures, ulcerations, eczema, and other pathological conditions of the anus and rectum. Such injectors include an outer sleeve-like body in which a medicament may be placed. The body has a drug delivery orifice at one end thereof and a plunger receiving portion at the other end thereof. An elongate plunger is fittable into the plunger receiving end of the body and is used to manually administer the drug through the drug delivery orifice by manually advancing the plunger through the body.

These rectal administrators have several disadvantages. First, the medicament must first be placed into the sleeve-like body before the elongate plunger can be fitted into the receiving end of the body (the administrators are not normally pre-filled). Because these administrators are not adapted for emergency use, the time constraints associated with filling the body with a medicament is of no consequence.

Second, even after the body of the conventional rectal administrator is filled with medicament, the user must still properly insert the separately provided elongate plunger into the receiving end of the body.

Third, even after the administrator is filled and arranged to have the forward end of the elongate plunger correctly aligned with the body, the total length of the assembly is quite long, requiring two hands to be used during the procedure of advancing the elongate plunger through the body; a first hand to grab the body and insert it into the rectum and a second hand to advance the plunger while the first hand maintains the body in place.

Fourth, even in the instance in which such an administrator may be manually pre-filled with medicament and pre-assembled with the elongate plunger positioned at the open end of the body, the total length of such an assembly would make it impractical to carry in one's pocket or the like.

Fifth, in the instance in which rectal diazepam is self administered, it can be appreciated that it would be quite difficult for a patient having a seizure, not only to insert the injector into his or her own rectum, but also to advance the plunger through the body to administer the drug.

Sixth, in the instance in which an adult is administering the drug into the rectum of a child, the time of such administration is limited by the need to manually advance the plunger through the body; a procedure which may take several valuable seconds.

Therefore, there exists a need for a compact, pre-filled rectal administrator having an automatic means of dispensing the medicament from the rectal administrator's body to facilitate the administrative procedure.

It is an object of the present invention to fulfill the need expressed above by providing an inexpensive rectal administrator which is adapted to automatically dispense medicament after being inserted into the user's rectum. In accordance with the principles of the present invention, this objective is achieved by providing a rectal administrator having a body with an administrative portion adapted to be inserted into a subject's anus. A charge of medicament is disposed within the body, and the administrative portion has at least one passage through which the medicament can exit the body. A plunger is disposed in the body and is movable from a first position to a second position within the body to dispense the medicament from the body through the at least one passage. A releasable energy source is mounted within the body so as to be released in response to a predetermined actuating procedure. The releasable energy source moves the plunger from the first position to the second position to dispense the medicament from the body through the at least one passage when released in response to the predetermined actuating procedure.

These and other objects of the present invention will become more apparent during the course of the following detailed description and claims.

The invention may be best understood with reference to the accompanying drawings wherein illustrative embodiments are shown.

BRIEF DESCRIPTION OF THE DRAWINGS

FIG. 1 is a longitudinal sectional view of one embodiment of the present invention in its storage position.

FIG. 2 is a longitudinal sectional view of the rectal administrator of FIG. 1 shown in its post-activated position.

FIG. 3 is a longitudinal sectional view of another embodiment of the present invention in its storage position.

FIG. 4 is a longitudinal sectional view of the rectal administrator of FIG. 3 shown in its post-activated position.

DETAILED DESCRIPTION OF THE PREFERRED EMBODIMENTS

FIG. 1 is a longitudinal sectional view showing an embodiment of the rectal administrator device according to the present invention prior to activation. The device comprises a cylindrical body 10 having an administrative portion 12 at its forward end. The administrative portion 12 is tapered as it extends towards its forward-most portion and has a forward end 11 smoothly contoured to facilitate insertion of the administrative portion into the rectum. The administrative portion 12 is provided with at least one laterally disposed drug dispensing passage 16 axially spaced from the forward extremity of the administrator. While only one passage is shown in FIG. 1, it can be seen in FIG. 2 that a plurality of passages 16 are preferably provided to allow a more disperse distribution of medicament.

The body 10 has an outer wall 18 from which an annularly disposed stopper 14 projects to separate the administrative portion 12 from the rest of body 10. Stopper 14 serves to limit the portion of body 10 which can be inserted into the anus to administrative portion 12.

A liquid or gel medicament 20 is filled within body 10 confined rearwardly by a piston or plunger 22, which is formed of resilient material and has an exterior periphery in sliding sealing engagement with the interior periphery 24 of body 10 in a position generally forwardly of the rear extremity thereof.

The medicament 20 is prevented from exiting through passages 16 before the automatic administrator is actuated by virtue of seal cap 26 which covers passages 16 when the injector is stored. Even with seal cap 26 removed, medicament 20 is kept within body 10, before being forced therefrom by plunger 22, by either air pressure exerted on medicament 20 through passages 16 from atmosphere, or by the sheer viscosity of medicament 20 (e.g., as is the case with petroleum jelly). For less viscous medicaments, it may be desirable to provide a thin impermeable membrane or wall 28 within body 10 to forwardly confine medicament 20 and to operate as a means for preventing the medicament from advancing through passages 16 before the device is actuated. Membrane 28 may be caused to rupture as a result of increased pressure of medicament 20 within body 10 when plunger 22 is released towards the forward end of the injector.

Spring assembly 30 which is constructed in accordance with the principles of the present invention includes a main rearward tubular housing member 32 having a forward annular ridge 34 formed on the exterior periphery thereof in rearwardly spaced relation to the forward end thereof and a rearward ridge 36 of slightly greater exterior diameter disposed in rearwardly spaced relation with respect to the forward ridge 34. The body 10 has the rearward interior periphery formed with an annular groove 38 so as to enable the rearward end portion of body 10 to be moved rearwardly over the forward end portion of the tubular housing member 32 of spring assembly 30 so as to be retained therein in a position in which the rearward extremity of the body 10 engages the forward surface of rearward annular ridge 36.

The tubular housing member 32 of spring assembly 30 is formed with an interior annular flange 40 spaced slightly inwardly from the rearward end thereof. The forward surface of the annular flange 40 is adapted to be engaged by a rearward volute of a coil spring 42 forming a part of the stressed spring assembly 30. Coil spring 42 operates as a releasable energy source for the present invention. It is understood that the present invention is not limited to the use of a coil spring and that another releasable energy source, such as an air spring, may be used. The forward volute of the coil spring 42 engages a rearwardly facing surface of a forward flange 44 of a collet member, generally indicated at 46.

The collet member 46 extends rearwardly from the forward flange 44 thereof within the coil spring 42. The rearward end portion of the collet member 46 is split so as to form a plurality (two) of rearwardly extending spring fingers 48. The spring fingers 48 shown are formed with a pair of oppositely facing rearward arcuate surfaces 50 which extend from the rearward extremity thereof inwardly and a pair of forward arcuate surfaces 52 of a slightly greater radius extending forwardly therefrom. The rearward peripheral portion of the fingers 48 are formed with radially outwardly extending arcuate flanges presenting forwarding facing locking surfaces 54 which are adapted to engage along a generally radially extending plane with the rearwardly facing surface of the interior annular flange 40 of the housing member 32. As shown, the locking surfaces 54 are disposed in a radial plane and the forwardly facing surface of the annular flange 40 has a slight angular extent, as for example, 16 degrees. It will be noted that the rearward peripheral portions of the spring fingers 48 also include frustoconical rearwardly and outwardly facing surfaces that cam the fingers 48 within the flange 40 during assembly.

As shown, a safety actuating pin member, generally indicated at 56, is disposed in cooperating relation with the resilient fingers 48 in a storage position and includes a forward portion 58 which is generally coextensive with the rearward arcuate surfaces 50 of the resilient fingers 48. The safety actuating member 56 also includes an intermediate portion 60 of a reduced diameter with respect to the forward portion 58, there being a frustoconical transition between the two portions. Formed on the forward portion adjacent the frustoconical transition is a series of annularly spaced threshold pressure inducing protrusions in the form of semi-spherical knobs 62 extending therefrom. The rearward extremity of the two spring fingers 48 of the collet member 46 are disposed forwardly of the knobs 62 and the forward extremity of the forward pin portion 58 is slightly enlarged to provide a retaining protrusion configured to enter beyond the arcuate surfaces 50 onto the forward arcuate surfaces 52 so as to prevent accidental rearward withdrawal of the safety actuating member 56. Finally, the safety actuating member 56 includes a rearward thumb-engaging or actuating portion 64 of an enlarged diametrical size. The thumb engaging portion 64 is of a size to engage within a corresponding capturing recess in the rearward interior periphery of the rearward housing member 32 rearwardly of the annular flange 40. It can be seen that when the locking surfaces 54 of the spring fingers 48 are engaged with the rearwardly facing locking surfaces of flange 40, the coil spring 42 is retained in a stressed condition between the forward flange 44 of the collet member 46 and the forwardly facing surface of the interior flange 40 of housing member 32.

As shown, cap structure 68, when in its storing position, covers actuating portion 64 and includes a tubular member 70 having a forwardly converging frustoconical section which terminates in a forward interior flange 72. Forward interior flange 72 is adapted to abut against the rearward surface of annular ridge 36 when cap structure 68 is in its storage position. Annular ridge 36 prevents interior flange 72 from sliding thereover so as to prevent actuating portion 64 from being depressed relative to body 10 of the injector. Thus, removal of cap structure 68 is required before actuation of this automatic injector can take place.

After the cap structure 68 has been removed, the user grasps body 10 in one hand and inserts the administrative portion 12 into the rectum. Next, the safety actuating pin member 56 which is in its storage position, as shown in FIG. 1, is moved forwardly by a thumb or other finger with pressure sufficient to overcome the threshold pressure provided by the engagement of knobs 62 with the fingers 48 until the actuating pin member reaches an actuating position adjacent arcuate surfaces 52. As the safety actuating pin member 56 reaches its forward actuating position adjacent arcuate surface 52, the spring fingers 48 flex by virtue of the pressure between the locking surface 54 and forward flange 44 so that their rearward ends move to a position approaching the surface of the intermediate portion 60 adjacent the thumb engaging portion 64. When the spring fingers have flexed to this extent, the locking surfaces 54 are moved off of the flange 40, allowing the collet member 46 together with the safety actuating pin member 56 to move forwardly under the action of the spring 42.

When the thumb engaging or actuating portion 64 of the safety actuating pin member reaches the flange 40, its movement is stopped and it is captured in the recess within the end of the tubular housing member 32, as shown in FIG. 2. However, as soon as the locking surfaces 54 have moved forwardly past the flange 40, the spring fingers 48 begin to unflex or move back into their storage position, as shown in FIG. 2. In this position the collet 46 continues to move forwardly while the safety actuating pin member 56 is left behind in captured relation by the tubular housing member 32.

The collet member 46 during its forward movement engages the piston or plunger 22. The continued movement of the plunger 22 towards the administrative portion 12 operates to pressurize the liquid medicament 20 causing the membrane 28 (if in place) to burst as a result of the increased pressure. The liquid medicament 20 then flows within administrative portion 12 and through passages 16 into the rectum of the user. The movement of the plunger 22 will continue until it reaches the necked down forward end 70 of body 10.

After the injection has thus been completed, the user withdraws the automatic rectal administrator from the rectum and then places the seal cap 26 over the administrative portion for sanitation purposes.

The seal cap 26 is capable of snapping into place so that it does not fall off administrative portion 12. This snapping action also provides a airtight seal so that medicament 20 is not exposed to atmospheric air when the rectal administrator is in storage.

The embodiment shown in FIGS. 3 and 4 is substantially similar to the previous embodiment with respect to the actuating mechanism of the injector. This embodiment differs, however, with respect to the administrative portion. In FIG. 3, the administrative portion 80 has the forward end 82 thereof operating as a receiving cup for movable plug member 84.

Movable plug member 84 replaces membrane 28 of the previous embodiment to forwardly contain medicament 20 and operate as a means for preventing the medicament from advancing through passages 86 before the device is actuated. During the forward movement of collet member 46 and plunger 22, medicament 20 is pressurized and forces plug member 84 forwardly into the administrative portion 80.

Plug member 84 continues forward in slidably sealed relation to an interior surface 90 of the administrative portion 80 until it passes passages 86 and is stopped by the interior surface 88 of forward end 82. After plug member passes passages 86, medicament 20 is free to exit the injector through passages 86. It can be appreciated that, while not shown in FIGS. 3 or 4, this second embodiment may be provided with a snap-fit cap such as seal cap 26 provided in the first embodiment. Such a sealing cap maintains the administrative portion in a sanitary condition prior to use and also serves to cover the administrative portion for disposal purposes after use.

It thus will be seen that the objects of this invention have been fully and effectively accomplished. It will be realized, however, that the foregoing preferred specific embodiment has been shown and described for the purpose of this invention and it is subject to change without departure from such principles. Therefore, this invention includes all modifications encompassed within the spirit and scope of the following claims.

What is claimed is:

1. A rectal administrator for dispensing anti-convulsant medication comprising:
   a body having an administrative portion adapted to be inserted into a subject's rectum;
   a charge of anti-convulsant medicament normally stored within said body, said administrative portion having at least one passage through which said anti-convulsant medicament can exit said body;
   a seal for normally obstructing communication between said stored charge of anti-convulsant medicament and air external to said body through said at least one passage, said seal being conditionable to permit said communication to facilitate administration of said medicament to said subject through said at least one passage;
   a plunger disposed in said body, said plunger being movable from a first position to a second position within said body to dispense said medicament from said body through said at least one passage;
   a releasable energy source mounted within said body for moving said plunger from said first position to said second position to dispense said medicament from said body through said at least one passage; and
   an actuating assembly constructed and arranged to release said releasable energy source so that said energy source moves said plunger from said first position to said second position to dispense said medicament.

2. The rectal administrator as claimed in claim 1 wherein said seal comprises a wall normally disposed between said medicament and said at least one passage.

3. The rectal administrator as claimed in claim 2, wherein said wall is conditionable by being ruptured in response to said plunger pressurizing said medicament.

4. The rectal administrator as claimed in claim 3, wherein said seal further comprises a removable seal cap for covering said administrative portion when said administrator is not in use.

5. The rectal administrator as claimed in claim 1, wherein said at least one passage is radially disposed with respect to a longitudinal axis of said administrator.

6. The rectal administrator as claimed in claim 5 wherein said at least one passage is axially spaced from a forward extremity of said administrative portion, and wherein said seal comprises a movable plug member fitted in slidably sealed relation with an interior surface of said administrative portion, said movable plug member being movable between a third position in which said movable plug member prevents said medicament from advancing through said passage and a fourth position in which said movable plug member permits said medicament to advance through said passage.

7. The rectal administrator as claimed in claim 1 wherein said seal comprises a removable seal cap for covering said administrative portion when said administrator is not in use.

8. The rectal administrator as claimed in claim 1 wherein said releasable energy source comprises a coil spring.

9. The rectal administrator as claimed in claim 1 wherein said actuating assembly includes means cooperable with said plunger for preventing movement thereof before said releasable energy source is released.

10. The rectal administrator as claimed in claim 1 wherein said anti-convulsant medicament comprises diazepam.

11. The rectal administrator as claimed in claim 1, wherein said seal comprises a movable plug member fitted in slidably sealed relation with an interior surface of said administrative portion, said movable plug member being movable between a position in which said movable plug member prevents said medicament from advancing through said passage and a position in which said movable plug member permits said medicament to advance through said passage.

12. The rectal administrator as claimed in claim 1, wherein said actuating assembly comprises a manually operable actuating member, said actuating member being manually movable to permit said releasable energy source to be released.

13. The rectal administrator as claimed in claim 1, wherein said seal comprises an impermeable membrane.

14. A rectal administrator for dispensing anti-convulsant medication comprising:
 a body having an administrative portion adapted to be inserted into a subject's rectum;
 a charge of anti-convulsant medicament normally stored within said body, said administrative portion having at least one passage through which said anti-convulsant medicament can exit said body;
 seal means for normally obstructing communication between said stored charge of medicament with air external to said body through said at least one passage, said seal means being conditionable to permit said medicament to be in communication with said air external to said body so as to facilitate administration of said medicament through said at least one passage;
 dispensing means disposed within said body for dispensing said medicament from said body through said at least one passage; and
 releasing means for enabling said dispensing means to dispense said medicament from said body through said at least one passage.

15. The rectal administrator as claimed in claim 14 wherein said seal means comprises a wall disposed between said medicament and said at least one passage.

16. The rectal administrator as claimed in claim 15, wherein said wall is conditionable by being ruptured in response to said dispensing means pressurizing said medicament.

17. The rectal administrator as claimed in claim 14 wherein said at least one passage is radially disposed with respect to a longitudinal axis of said administrator.

18. The rectal administrator as claimed in claim 17 wherein said at least one passage is axially spaced from a forward extremity of said administrative portion, and wherein said seal means comprises a movable plug member fitted in slidably sealed relation with an interior surface of said administrative portion, said movable plug member being movable between a first position in which said movable plug member prevents said medicament from advancing through said passage and a second position in which said movable plug member permits said medicament to advance through said passage.

19. The rectal administrator as claimed in claim 14 wherein said seal means comprises a removable seal cap for covering said administrative portion when said administrator is not in use.

20. The rectal administrator as claimed in claim 14 further comprising a restraining assembly operable to prevent said releasing means from enabling said dispensing means to dispense said medicament from said body through said at least one passage.

21. The rectal administrator as claimed in claim 14, wherein said releasing means comprises an normally compressed coil spring, said coil spring being releasable to enable said dispensing means to dispense said medicament from said body through said at least one passage.

22. A device for rectally administering a medicament used for treating an emergency condition comprising:
 a body having an administrative portion adapted to be inserted into a subject's rectum;
 a charge of medicament normally stored within said body and especially formulated to be absorbed into the subject's bloodstream through walls of the rectum to treat an emergency condition, said administrative portion having at least one passage through which said medicament can exit said body;
 a seal for normally obstructing communication between said stored charge of medicament and air external to said body through said at least one passage, said seal being conditionable to permit said communication to facilitate administration of said medicament to said subject through said at least one passage;
 a plunger disposed in said body, said plunger being movable from a first position to a second position within said body to dispense said medicament from said body through said at least one passage;
 a releasable energy source mounted within said body for moving said plunger from said first position to said second position to dispense said medicament from said body through said at least one passage; and an actuating assembly constructed and arranged to release said releasable energy source so that said energy source moves said plunger from said first position to said second position to dispense said medicament.

23. The device of claim 22, wherein said medicament comprises an anti-convulsant.

24. The device of claim 23, wherein said medicament comprises diazepam.

25. A rectal administrator comprising:

a body having an administrative portion adapted to be inserted into a subject's rectum;

a charge of medicament normally stored within said body, said administrative portion having at least one passage through which said medicament can exit said body;

a seal member disposed within said body and movable within said body in slidably sealed relation with respect to an interior surface of said administrative portion from a position in which said seal member prevents said medicament from advancing through said passage to a position in which said seal member permits said medicament to advance through said passage;

a plunger disposed in said body, said plunger being movable from a first position to a second position within said body to dispense said medicament from said body through said at least one passage;

a releasable energy source mounted within said body for moving said plunger from said first position to said second position to dispense said medicament from said body through said at least one passage; and an actuating assembly constructed and arranged to release said releasable energy source so that said energy source moves said plunger from said first position to said second position to dispense said medicament.

* * * * *